United States Patent
Neal

(10) Patent No.: US 12,036,047 B1
(45) Date of Patent: Jul. 16, 2024

(54) SINGLE USE DISPOSABLE POP-UP MEDICAL CART

(71) Applicant: TAGCarts, Inc., Sacramento, CA (US)

(72) Inventor: Taggart Neal, El Dorado Hills, CA (US)

(73) Assignee: TAGCARTS, INC., El Dorado Hills, CA (US)

( * ) Notice: Subject to any disclaimer, the term of this patent is extended or adjusted under 35 U.S.C. 154(b) by 605 days.

(21) Appl. No.: 17/218,644

(22) Filed: Mar. 31, 2021

Related U.S. Application Data

(60) Provisional application No. 63/003,031, filed on Mar. 31, 2020.

(51) Int. Cl.
| | |
|---|---|
| *A61B 50/13* | (2016.01) |
| *A47B 43/02* | (2006.01) |
| *A61B 50/10* | (2016.01) |
| *A61B 50/18* | (2016.01) |
| *B65D 5/22* | (2006.01) |
| *B65D 5/38* | (2006.01) |

(52) U.S. Cl.
CPC ............. *A61B 50/13* (2016.02); *A47B 43/02* (2013.01); *B65D 5/22* (2013.01); *B65D 5/38* (2013.01); *A61B 2050/105* (2016.02); *A61B 2050/185* (2016.02); *A61B 2560/0285* (2013.01); *A61B 2560/0431* (2013.01)

(58) Field of Classification Search
CPC ......... A47B 43/02; A47B 43/00; A47B 46/00; B65D 5/38; A61B 50/13; A61B 2050/105; A61B 2050/185; A61B 2560/0285; A61B 2560/0431
See application file for complete search history.

(56) References Cited

U.S. PATENT DOCUMENTS

| | | | | |
|---|---|---|---|---|
| 4,437,713 | A * | 3/1984 | Roach | B65D 5/38 229/122 |
| 5,904,410 | A * | 5/1999 | Davies | A47B 43/02 312/258 |
| 6,126,254 | A * | 10/2000 | Maglione | A47F 5/116 312/259 |
| 11,019,943 | B2 * | 6/2021 | Burgert | A47F 5/116 |
| 11,478,076 | B2 * | 10/2022 | Gibbons, Jr. | A47F 5/116 |
| 2006/0226746 | A1 * | 10/2006 | Kopenhaver | A47B 67/00 312/330.1 |

(Continued)

*Primary Examiner* — Daniel J Rohrhoff
(74) *Attorney, Agent, or Firm* — Heisler & Associates

(57) ABSTRACT

A cabinet and multiple drawers are originally provided in a collapsed configuration with multiple separate walls, layers and plates connected together, such as through bendable creases. Folding along the creases causes a cabinet sheet to be reconfigured into a deployed cabinet with multiple recesses for receiving drawers therein. A topper can be placed on top of the cabinet. Wheel assemblies can be attached to a bottom of the cabinet. A drawer sheet including multiple separate layers and walls separated by creases can similarly be folded to be erected into a deployed drawer which fits into one of the recesses in the cabinet. A wheeled base can optionally be provided as a multi-wheel assembly upon which the bottom of the cabinet can rest. The cabinet and/or drawers can be partially pre-assembled and optionally spring-loaded to pop-up from a collapsed planar configuration to a deployed configuration.

18 Claims, 11 Drawing Sheets

(56) References Cited

U.S. PATENT DOCUMENTS

| | | | |
|---|---|---|---|
| 2006/0290244 A1* | 12/2006 | Wang | A47B 87/0276 |
| | | | 312/3 |
| 2007/0176525 A1* | 8/2007 | Yoon | A47B 67/04 |
| | | | 312/258 |
| 2013/0213915 A1* | 8/2013 | Pfeifer | A47F 5/116 |
| | | | 211/195 |
| 2015/0305521 A1* | 10/2015 | Volz | A47F 5/116 |
| | | | 211/186 |
| 2017/0231404 A1* | 8/2017 | Pratsch, Jr. | A47F 5/116 |
| | | | 211/135 |
| 2019/0069694 A1* | 3/2019 | Smith | A47B 55/06 |
| 2019/0350383 A1* | 11/2019 | Bersamin | A47F 5/116 |
| 2020/0077816 A1* | 3/2020 | Doane | A47B 43/02 |
| 2020/0375375 A1* | 12/2020 | Robinson | A47B 55/06 |

* cited by examiner

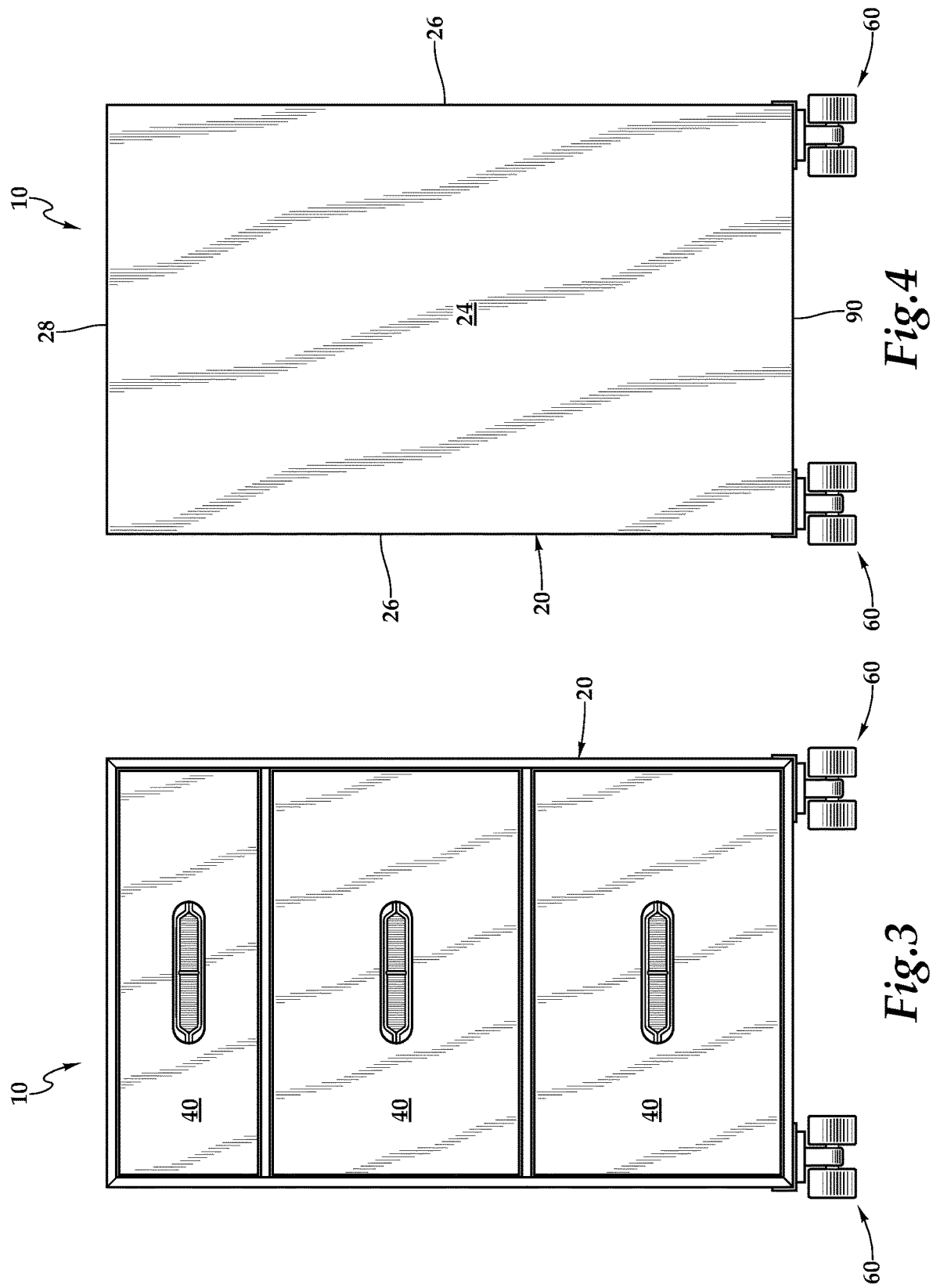

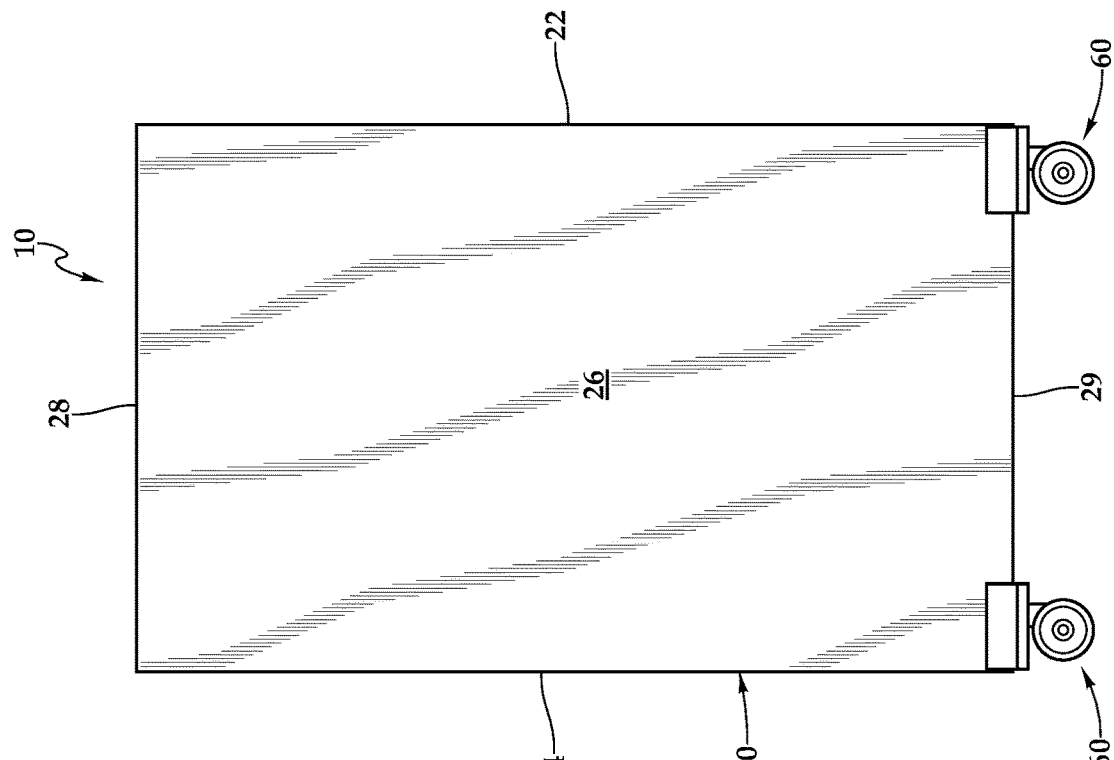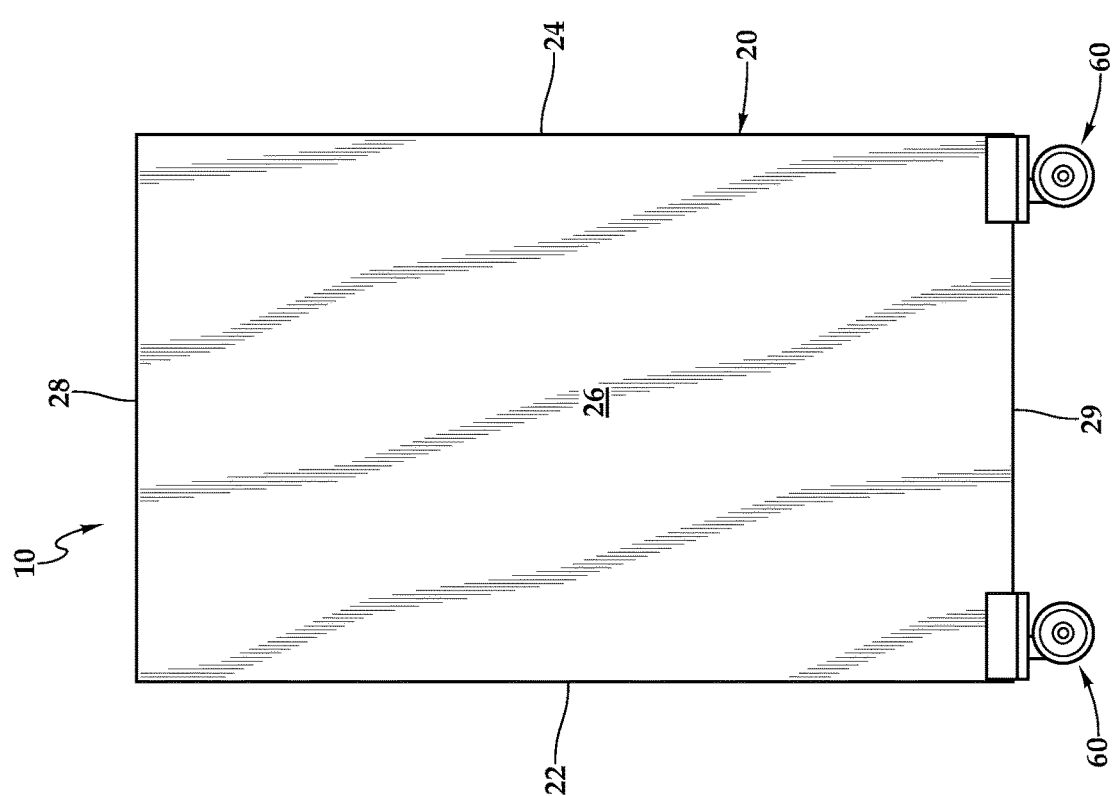

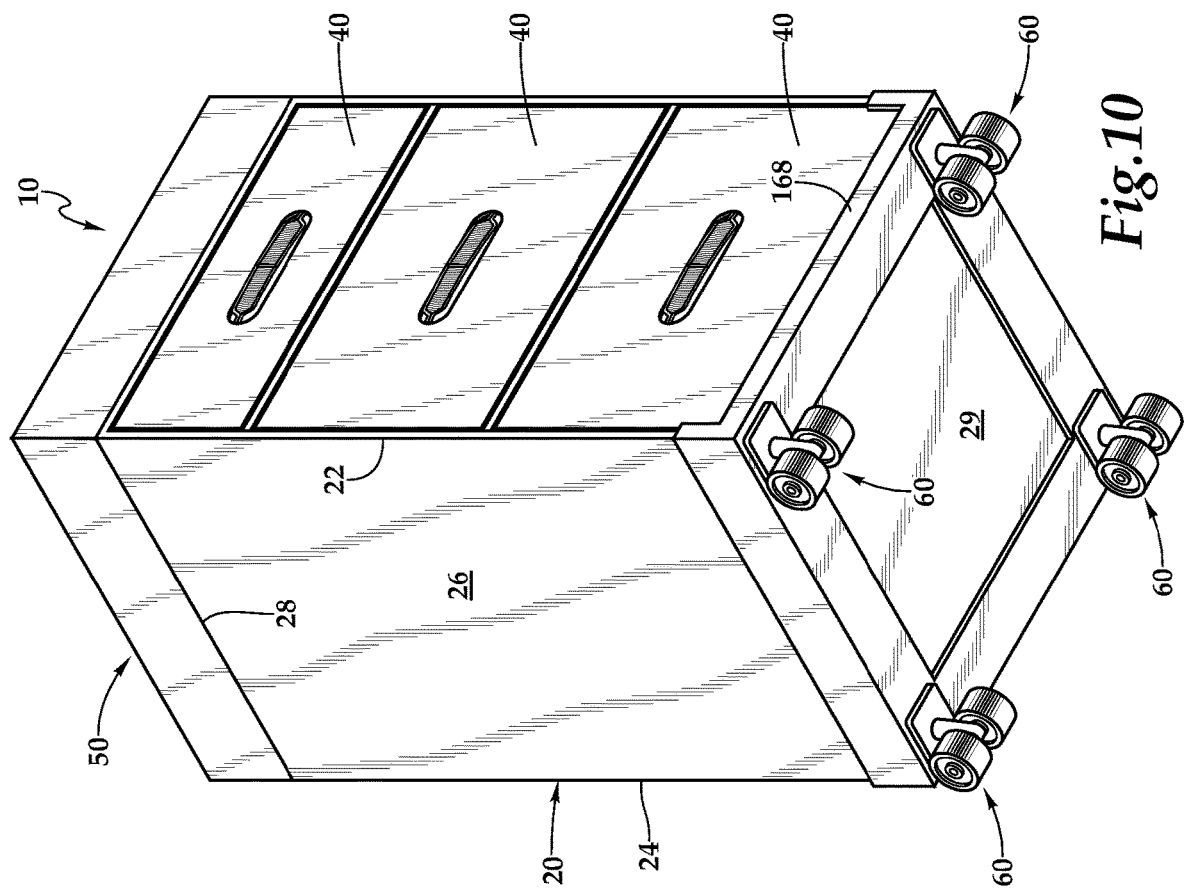
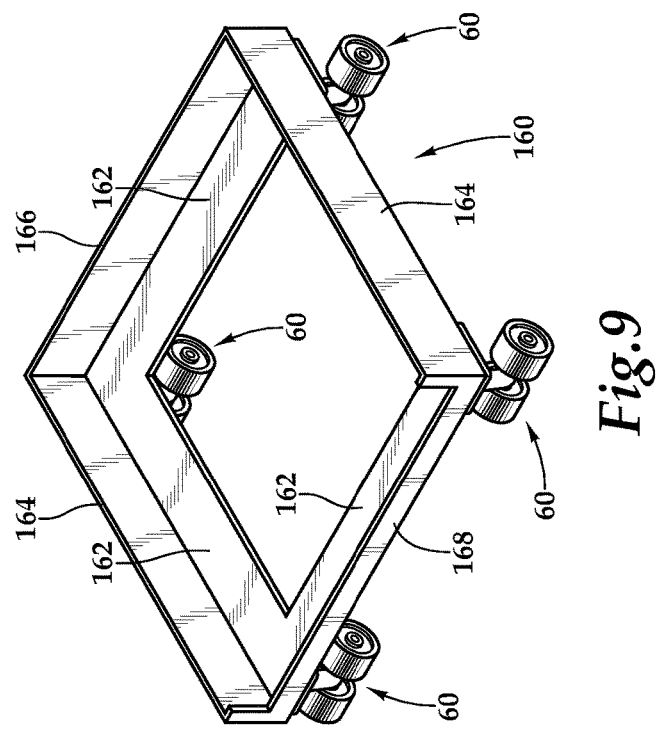
*Fig.10*
*Fig.9*

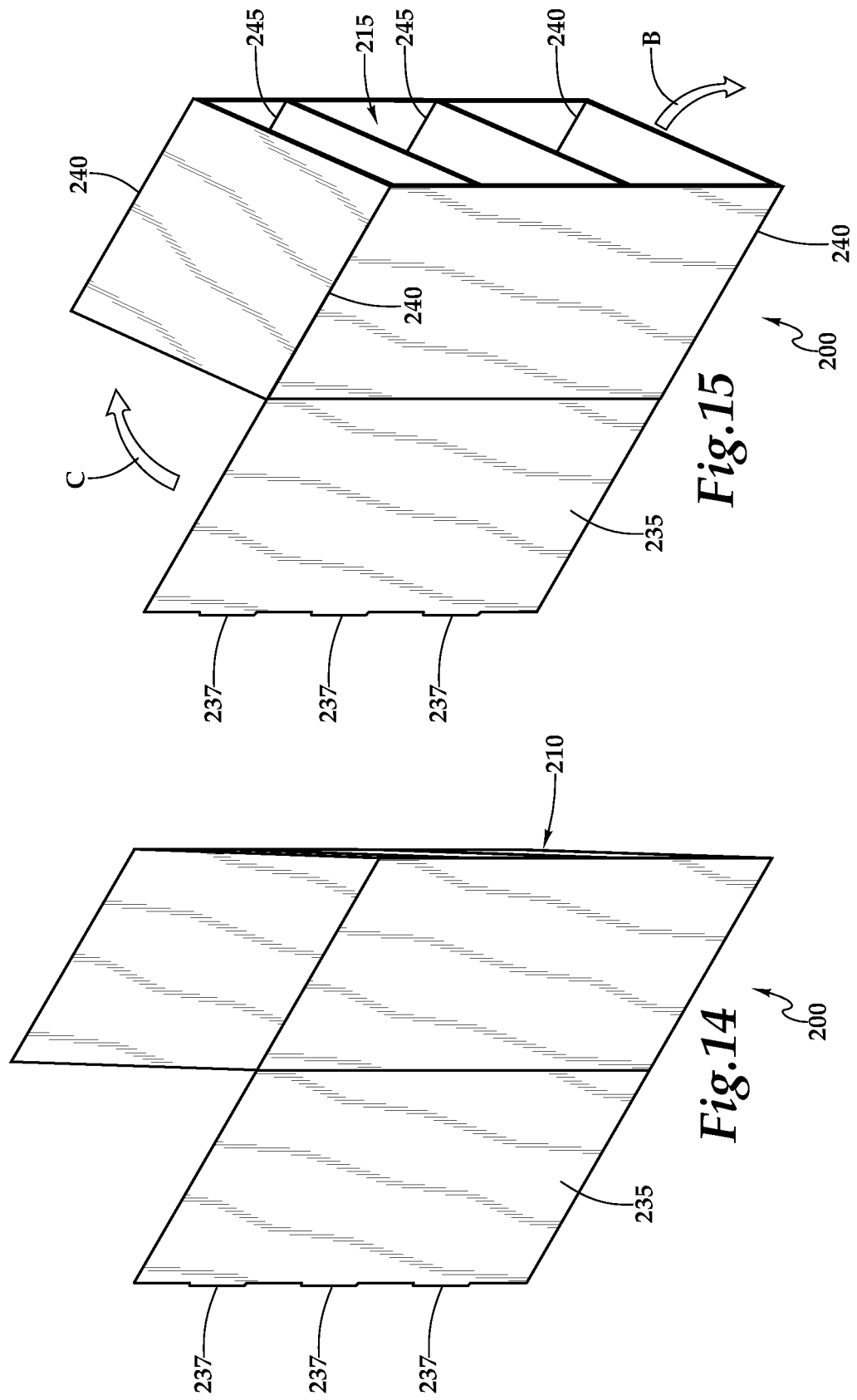

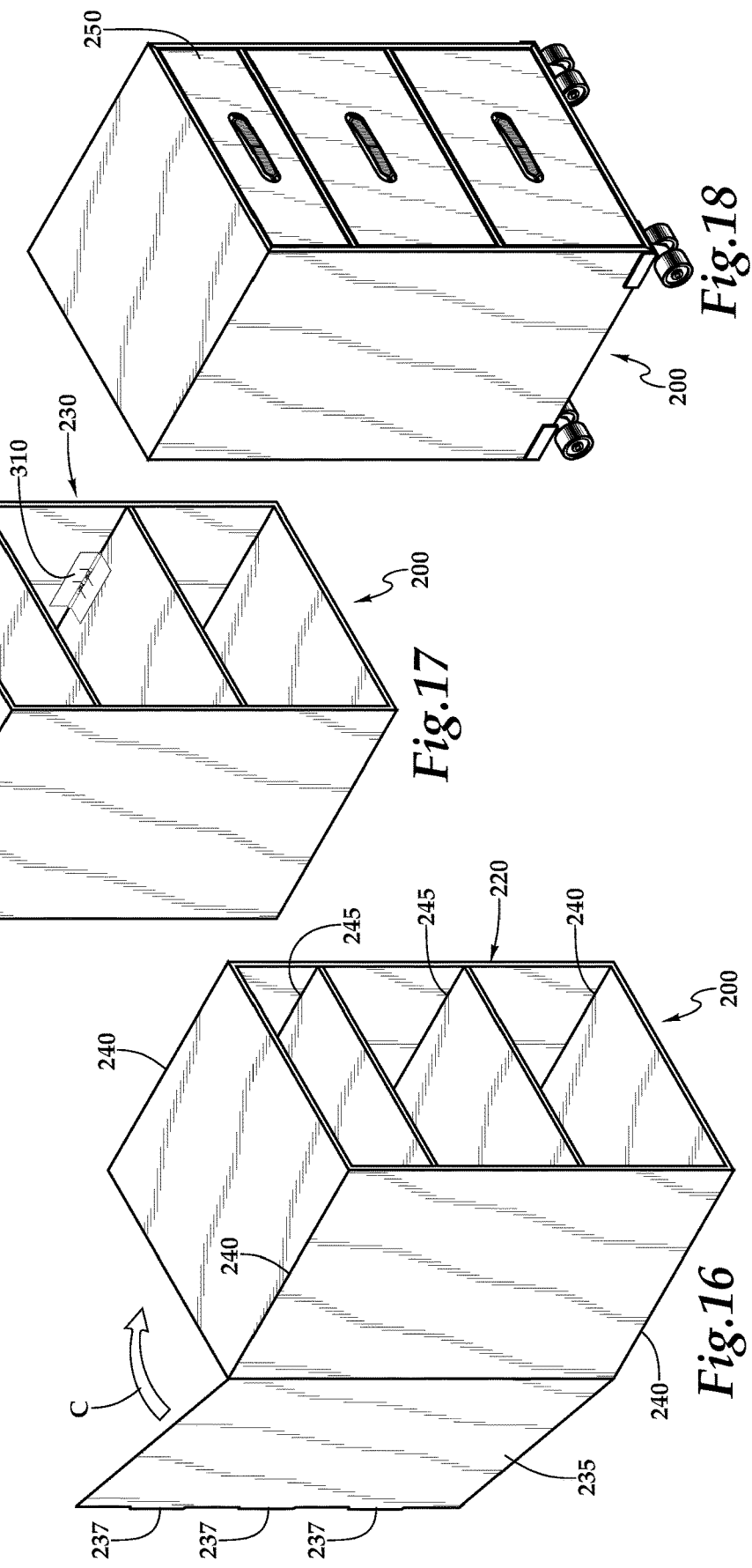

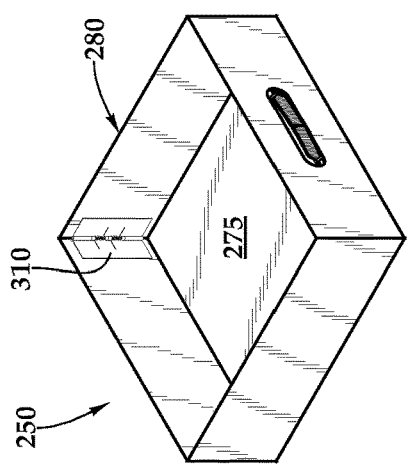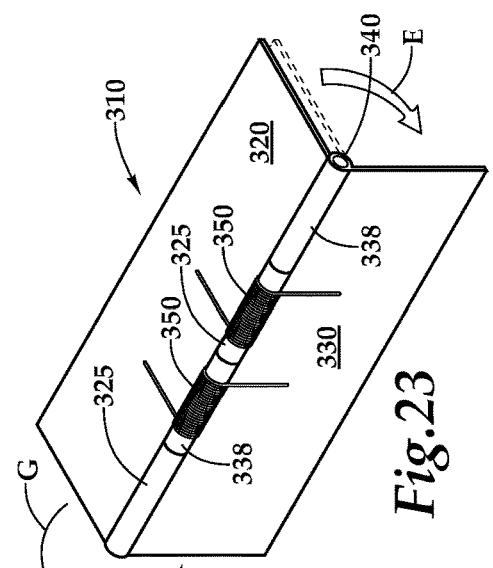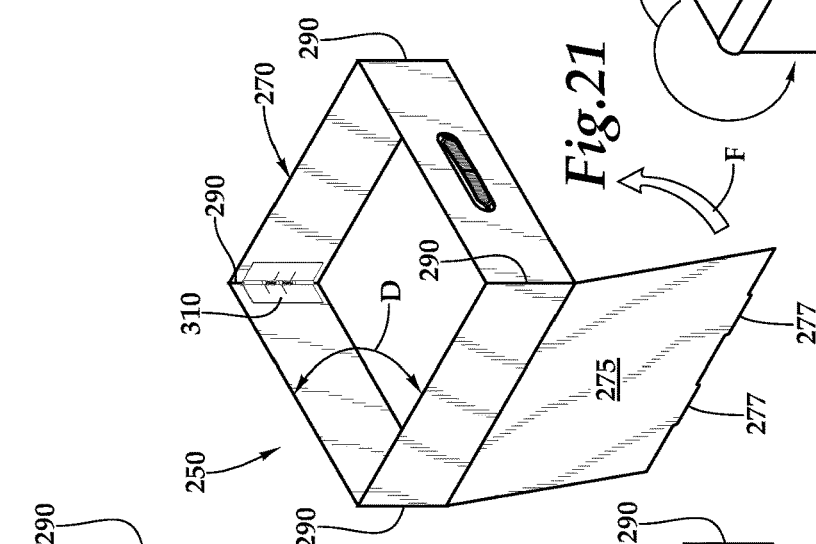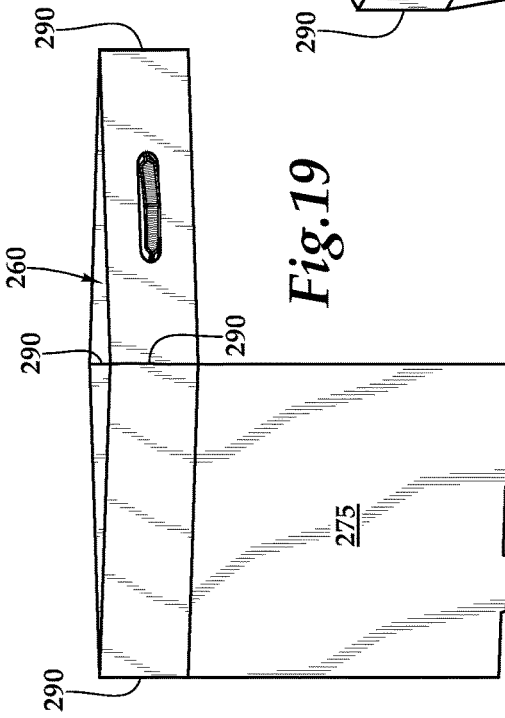

SINGLE USE DISPOSABLE POP-UP MEDICAL CART

CROSS-REFERENCE TO RELATED APPLICATIONS

This application claims benefit under Title 35, United States Code § 119(e) of U.S. Provisional Application No. 63/003,031 filed on Mar. 31, 2020.

FIELD OF THE INVENTION

The following invention relates to carts for use in medical environments with wheels on lower portions thereof to facilitate cart mobility and with at least one drawer located within a cabinet. More particularly, this invention relates to medical carts which are transitioned between a collapsed and a deployed configuration for compact storage during shipping and when not in use, and which carts can be made of disposable and/or biodegradable materials to facilitate convenient single use, and without requiring re-sanitization.

BACKGROUND OF THE INVENTION

In hospitals and other medical environments (including temporary, non-traditional environments of care (EOC)) medical carts have become highly useful to support the work of medical practitioners. Medical carts can store personal protective equipment (PPE), portable diagnostic equipment, medications, patient record documents, computers and other electronic devices (which may or may not access a patient support data network) and a nearly limitless assortment of other supplies and equipment. By placing the most commonly used items on such a cart, and because the medical environment already has hard floors for supporting wheeled structures such as hospital beds and other portable equipment, the medical cart provides a convenient way to keep these items in an easily accessible location close to where they are needed and mobile to deliver care to a patient's location, rather than bringing the patient to the supplies or equipment to be used.

Typical medical carts include a wheeled base and a stand extending up from this wheeled base, with various different structures coupled to this stand which are provided to maximize the usefulness of the cart. Some carts can be general purpose including a combination of drawers for containing items, as well as surfaces upon which items can be rested, and arms which support computer monitors, etc. in various locations. Other medical carts can be special purpose carts, such as a medication cart which primarily only houses medications and associated equipment. Because the cart is on wheels, a medical practitioner can keep the cart close by so that items contained or supported by the cart are immediately available when needed. The cart can keep these items sanitary, keep these items close to the medical practitioner to avoid extra travel and time for the medical practitioner (to otherwise retrieve necessary items), and can keep items secure, especially items which are prone to theft or misuse, or are fairly commonly misplaced. Carts can also be used as a patient bedside accessory.

Existing prior art medical carts are generally in the category of durable medical equipment or perhaps categorized as capital assets of a hospital or other medical facility. The medical carts are expected to be maintained and used and reused for a significant period of time (typically years of useful life). With such a paradigm, medical carts benefit from being easy to sterilize periodically and emphasis is placed on durability. Materials are selected which are both durable and easy to sanitize. While these are generally desirable characteristics, they also add weight and expense to the medical cart. Shifting away from the durable medical equipment to single use/disposable would avoid these drawbacks and facilitate billing of the cart expense to the patient.

Typical prior medical carts are constructed in advance and delivered to a hospital or other medical facility in an already assembled state. If any assembly is required, typically this assembly is somewhat complex and time-consuming, to allow the finished product to have the requisite durability. Because the pre-constructed medical carts take up a relatively large amount of space, an amount of carts which can be held in inventory/storage is less than it would be if the carts had a first collapsed form and a second deployed form. Accordingly, a need exists for a collapsible medical cart which can minimize storage space required per cart, and maximize a number of carts which can be held in a given amount of storage space, and yet be deployed rapidly by transitioning into a usable deployed configuration. Such storage space can be on site at a hospital or other medical facility, or can be at some other inventory location such as inventory of a cart manufacturer or inventory of a holder of emergency medical equipment and supplies, such as an agency of the military or various different emergency management and disaster response agencies.

In medical emergencies, medical personnel must often make compromises between the very best equipment being selected to perform medical care and selecting equipment which is "good enough" and which can be more rapidly put into use, and otherwise has characteristics suitable for medical emergencies. Some medical emergencies have an infectious disease component where risk of disease transmission is significantly elevated.

In many such medical emergencies typical prior art medical carts are not particularly useful. Such prior art medical carts typically require a power source, which may not be available in a temporary hospital location (as well as mass population locations where care, hygiene or wellness may enhance total environment through mass distribution carts for individuals, groups or cohorts based upon symptoms, levels of wellness or other criteria). Such typical prior art medical carts are not readily storable in volume and/or easily transported to where they are needed, due to their size and weight. Such typical prior art medical carts typically have multiple complex surfaces which can be difficult to fully sterilize, and thus present a risk of disease transmission which is undesirable, and may call for more complex disinfection procedures which might not be available in many circumstances, and especially emergencies. Also, more complex carts present a heightened risk of cross-contamination when these carts are together providing many different goods, supplies, medications, bedding, hygiene items and wound care items to multiple patients. By instead providing distinct carts for distinct purposes, and separate from each other, information risk is mitigated.

Accordingly, a need exists for a cart which can be rapidly deployed from a compact collapsed orientation into a deployed orientation. Such a cart can address the need for a basic medical cart which avoids the need for complex sterilization procedures and which can still provide many of the benefits of a medical cart for use in hospitals and medical facilities, and especially in emergency hospital environments or non-hospital spaces which are being temporarily converted into use as hospital space or other mass population environments where care, wellness, temperature relief or care items benefit the whole group or population. Such a cart would beneficially be recyclable or biodegradable/compostable, to allow for sustainable disposal or recycling, especially after as few as a single use. Such a cart can be packaged, wrapped and/or treated in such a way as to be aseptic or sterile, reducing or eliminating risk of transmission of contaminates or bacteria, or other disease agents to individual patients. Rather, such a cart can be first used in sterile form for patients and especially high risk patients, such as burn victims or others with compromised immune systems.

SUMMARY OF THE INVENTION

With this invention, a medical cart is provided which is configured to be primarily a single use cart formed of materials which are at least recyclable, and preferably compostable and/or biodegradable (and can additionally be made of recyclable material or sustainable material to reduce the overall carbon footprint of the cart). These attributes, considered as a whole, can generally be referred to as "sustainability." The medical cart furthermore is configured to have a collapsed form and a deployed form. The collapsed form is preferably comprised of one or more thin sheets of material. These sheets of material can be strategically folded in a simple fashion to cause the medical cart to be deployed from its collapsed form. Details of suitable materials for the medical cart and configurations for the medical cart and attributes of the medical cart are provided with reference to an exemplary embodiment disclosed herein, as well as through various alternatives and examples disclosed herein, which describe some of the embodiments of this invention.

The medical cart is preferably formed from a series of planar elements. These planar elements can be provided in a collapsed form as sheets. Most preferably, these sheets have bend/fold lines and/or creases (or perforations or other zones of weakness) built therein, which facilitate bends in the sheets of material at strategic locations. In one embodiment, such bend/fold lines are compressed, perforated, or otherwise scored to facilitate a bend, typically a 90° bend or a 180° bend of the material at the bend/fold lines.

The material forming the sheets could be a recyclable plastic material (or recycled organic plastic resin, such as bamboo, hemp or post consumer recycled material (such as water bottles harvested from ocean debris or waterways or landfills, etc.)). In one embodiment, plastic of a thin planar lightweight nature is provided, which plastic is provided with front and rear planar sheets and with a fluted undulating layer between the front and rear planar sheets, generally similar to how many cardboard boxes are constructed, but when made of plastic, such as polyethylene, is able to be recycled. Another option for the material would be a plastic material which is biodegradable/compostable.

In another embodiment, the material forming the sheets from which the medical cart is constructed could be cardboard sheets with at least a front and rear layer and with an undulating middle layer therebetween, and as an option, having many such alternating layers therein. As with the plastic embodiment described above, score lines, perforations, indentations, crimping and/or other alterations to the otherwise homogenous sheets of the material can be provided along bend/fold lines to facilitate bending of these sheets of material at these locations, such as with a 90° or 180° bend.

In one embodiment, multiple such sheets provide different parts of the medical cart. These sheets could be parts of as few as just one sheet, or could be a stack of sheets (e.g. five sheets) that make up one medical cart. For instance, one medical cart such as that shown in the included drawings generally is in the form of a cabinet with shelves, and with three drawers (as an example) which fit upon the shelves. Four or five sheets of material (which could be provided on portions of a single sheet originally) would allow one medical cart with three drawers to be formed. One sheet of material would fold into the cabinet. The other three (as an example) sheets of material would form the three drawers which fit upon the shelves of the cabinet. A fifth sheet can fold into a top walled tray resting upon or attached to a top of the cabinet. In alternative embodiments, different numbers of shelves and drawers could be provided. The cabinet and/or shelves would be constructed by folding along the bend/fold lines to convert the planar sheets into the three dimensional objects (the cabinets and/or the drawers and optional tray) to complete the overall cart construction.

As a second option, the entire medical cart, or at least different components of the medical cart can be formed so that they transition from the collapsed form to the deployed form in a "pop-up" fashion. As an example, the medical cart having the four parts, including the cabinet part, and three drawer parts would be provided originally as four collapsed separate sheet assemblies. The cabinet sheet assembly would have two main parts, with the first part being a planar back wall of the cabinet, and with the second part being the various shelves and left and right vertical sides of the cabinet. A third part could optionally be provided which would be in the form of a planar base layer. A lowermost shelf of the cabinet could alternatively be this planar base layer.

The two vertical side walls of the cabinet would be attached at lower edges thereof to this planar base layer, and would be folded into a collapsed position parallel and adjacent with the base layer. Shelves between the two sidewalls would be attached in a pivoting fashion at desired locations on the two sidewalls, so that when the sidewalls are pivoted into an orientation perpendicular with the base layer (or lower shelf of the cabinet) the shelves would also pivot to remain parallel with the base layer (or lower shelf).

Once the sidewalls are perpendicular to the base layer (or lower shelf), the first part in the form of the planer back wall would have a lowermost edge thereof pivotably attached to the base layer (or lowermost shelf), that would be pivoted up to a perpendicular orientation, where it would be brought adjacent to back edges of each of the sidewalls and each of the shelves. Some form of fasteners (adhesive, clips, zip-ties, or other fasteners) would allow the planar back wall first part and the shelves and side wall second part to join together to complete the formation of the cabinet. With such a form, the cabinet of the medical cart could essentially "pop-up" by merely pivoting the two main parts relative to the base layer (or lowermost shelf) and then fastening them together.

Similarly, each of the drawers could be configured to "pop-up" by having the floor of each shelf be the one main part and having the side walls and front and rear walls hinged together as a second part. One of these front or rear walls provide the base layer about which the main parts pivot before attaching together to complete the construction. Fastening of the floor of each drawer to the front, rear and sides of each drawer (with appropriate fasteners) would complete the formation of each drawer. The drawers could then be placed upon the shelves in the cabinet portion to complete the medical cart. Triggering the deployment of such a pop-up cart could occur by pulling a string or strings to remove collapsed orientation retainers, or removal of wrapping which holds the cart in its collapsed configuration.

Further accessorization of the medical cart could include addition of handle structures to front portions of each drawer. A walled tray can similarly be formed and coupled to a top surface of the pop-up medical cart if desired.

Preferably, wheels are provided on a lowermost portion of the cabinet to allow the medical cart to be easily moved about upon a floor surface. In on embodiment, caster wheels are provided and these wheels are pre-fabricated as caster wheel kits both rotationally and pivotally mounted to a base plate. This base plate could be adhesively attached (or otherwise fastened) to an under surface of the cabinet portion of the medical cart. It is also conceivable that the medical cart could merely be skidded around on a flat surface, and be provided without wheels. Nubs or short posts, such as of plastic or a low friction hardened material could also be an option to facilitate skidding movement, and stability when stationary. The nubs/posts could attach like the wheels, through adhesive or other fasteners, and extend down to a smooth hard lower surface. The wheels can be configured to move between a collapsed and a deployed position as well, responsive to pulling a string or other actuation input to cause a fold-out or pop-out wheel deployment.

The same methodology which is used to deploy the drawers and cabinet of the medical cart could be reversed to allow for collapsing of the medical cart from the deployed orientation to the collapsed orientation, such as during initial construction. If the medical carts are deployed, but then not put into use with a patient or otherwise used in a usage environment, and it is desired to return the medical carts into a low volume storage orientation they can be re-collapsed. If desired, each of the planar sheets could be contained together within a single package, such as plastic wrap, straps, a box, or other enclosure, which could also contain the caster wheel assemblies and any other accessories such as handles. The package could be sanitary, aseptic or sterile on an interior and exterior, such as by sterile treatment prior to packaging, then individually packaged to maintain the sterile integrity of the cart, guaranteeing sterility for individual patient use upon integration and deployment, so that the medical cart is sanitary before deployment and use.

In a typical embodiment, the pop-up medical carts would be provided without contents therefore. A user, after deploying the medical cart, could then fill the drawers with appropriate equipment for use with the medical cart. If desired, packages of useful medical equipment could be prepackaged or kitted supplies within enclosures or environments which fit neatly into the drawers of the medical cart. Thus, equipment to be contained within the medical cart could be rapidly inserted therein and be already sized to fit within the drawers and maximize usable space.

As an example, a lowermost drawer could contain one form of personal protective equipment, such as sterile disposable gowns in a sealed package sized to fit in the lower drawer. A second drawer could contain a package of personal protective equipment such as in the form of boxes of surgical gloves and boxes of face masks, shoe covers, head covers, etc., all in a pre-sealed package sized to fit in the second drawer. The top drawer could be left empty and could be usable to contain a patient's personal items or various other items. The sealed packages can have labels that can be removed from the packages and adhesively attached to fronts of the drawers, so that precise drawer contents are accurately displayed in detail.

In one embodiment, an extra layer of planar material is configured as a cover structure for a top of the cart to rest upon an upper surface of the medical cart, optionally with side walls, and optionally to fasten securely to the cabinet. This uppermost layer can have a smooth top surface (optionally coated or lined with an easily cleanable (or removal and disposable liner) which can be easily wiped clean, and which can provide a sterile surface upon which items can be placed which need to remain sterile. This surface could be formed of a material which is inherently less conducive to infectious agent life. Such a top surface could be color-coded and different medical carts could be provided which are being used for different purposes, and the color coding can be utilized to coordinate and deploy the medical carts most effectively to service the needs of particular different patients. This cover structure can be configured to add rigidity to the cart and/or to be a removable structure to protect the rest of the cart.

The entire cart (or parts) can be given a sterile coating or be lined with a sterile layer. The entire cart (or parts) can be sprayed, treated, coated or wrapped so that anti-microbial (and/or anti-bacterial) surface areas are achieved. The cart is thus less conducive to infectiousness.

Surfaces of the cart can be printed with colors, codes or other indicia that organize the carts by particular use. The printing could be simple or complex. As an example, yellow carts might be "isolation carts" configured to contain isolation gear, green carts could be for anesthesia and/or airway support equipment, red could be for a "crash cart" or fire related gear and blue could be for a basic bedside/cot side cart. Other printing or other exterior appearance can be provided to be aesthetically pleasing, such as themes of nature, wellness, patriotism, sports, pop-culture icons, licenses images, logos, etc.

While a most basic medical cart is disclosed herein, more complex medical cart accessories could additionally be provided. The medical cart could be scaled to larger sizes than those indicated herein. The medical carts could be configured to contain a battery power supply which could power various different devices, such as with outputs for charging of cell phones, powering of laptop computers, and providing power for operation of or recharging batteries of various different portable medical equipment items. The lower drawer could be replaced or resized to leave space on the lower shelf/base plate of the cabinet for the battery and/or other heavy equipment.

The carts could be fitted to allow for support of medical equipment such as IV (i.e. intravenous) poles (formed of traditional or recyclable/compostable materials to support sustainable disposability), various forms of respiratory support equipment, medication dispensing compartments, defibrillators, basic physical examination gear, computer monitor, laptop computer and/or keyboard in any other of a variety of different configurations to give the pop-up medical cart as much usefulness as possible (which equipment can, as an option, be at least partially recyclable and/or sustainably disposable). Requisite strength attributes can be added to allow such gear to be securely supported. For instance, an IV pole can fit vertically through holes in the planner horizontal layers of the cabinet, optionally with bushings to strength the holes. Such holes can be at a rear corner and the drawers sized/shaped to give clearance for an IV pole passing through such holes. Similarly, respiratory support gear and computer monitors can be supported on pedestals supported by the cart through the same corner holes and bushings used for IV poles. Thus, the medical carts can have a more complex form and function as workstation medical carts.

Most preferably, after the medical cart has been used with a patient, any unused contents of the medical cart which remain within sanitary enclosures can be removed from the medical cart, and the medical cart can be collapsed and then recycled or disposed of. As an alternative, the cart could be sanitized and reused at a care facility, or sent home with the patient. The medical cart will have a compact collapsed form while being transported and otherwise handled before recycling and/or disposal. Whether recycled or disposed of, no disinfection or other sterilization processes are required because the medical cart is not reused within a medical environment. Rather, the medical cart would be handled generally in accordance with biohazard material of a similar nature until recycling and/or disposal has been achieved.

The included drawings illustrate variation on one embodiment for the medical cart of this invention both in an exemplary assembled form, and showing sheets with patterns thereon, indicating one configuration for the cabinet and drawers of such a medical cart. The medical cart could be used bedside or cot side primarily, or could be moved about with a medical professional to be available for use by that professional. Larger carts could act as supply carts to replenish smaller cot-side or bedside carts. The collapsible and lightweight nature of the medical cart allows for large stockpiles of collapsed medical carts to be held in reserve to meet emergency surge capacity needs. Such stockpiles could be palletized for easy handling, preloaded into shipping or storage containers, etc., until they are needed, and deployable on demand.

As another option, the deployable medical cart can exist as a "print file" for use by a cardboard (or other material) printer, so that carts can merely be "printed" on demand when needed. A printer and a stockpile of cardboard would be the only items stored. The printer could be part of a perforation or die cutting or other cutting machine to further allow for sheet preparation to facilitate bending and deployment of the medical cart. Alternatively, a printer and a cutter could be separate machines used sequentially. A hospital or other EOC can have a location, such as a basement, to house such a printer and cardboard stockpile ready for use on demand to create carts as needed.

OBJECTS OF THE INVENTION

Accordingly, a primary object of the present invention is to provide a medical cart which transitions between a smaller volume collapsed configuration and a larger volume deployed configuration.

Another object of the present invention is to provide a medical cart which is conveniently configured to facilitate single use, such that sanitization procedures are minimized or avoided while sterility is maintained.

Another object of the present invention is to provide a medical cart which is formed of biodegradable and/or compostable, disposable materials.

Another object of the present invention is to provide a medical cart which includes a disposable cabinet and disposable drawers which cabinet and/or drawers can be transitioned between a collapsed configuration and a deployed configuration.

Another object of the present invention is to provide a disposable medical cart which includes a wheeled base upon which the cabinet can rest, which wheeled base can be re-used with other disposable cabinets.

Another object of the present invention is to provide a medical cart having a collapsed configuration and a deployed configuration, and which transitions between configurations in an at least partially automated fashion for fast and convenient transition of the medical cart from its collapsed configuration to its deployed configuration.

Another object of the present invention is to provide a medical cart which is of low cost to manufacture and assemble.

Another object of the present invention is to provide a collapsed medical cart which is easy to erect into a usable configuration.

Another object of the present invention is to provide medical cart which at least partially erects itself into a usable configuration.

Another object of the present invention is provide a medical cart which can be stored in an exceptionally small volume when not in use.

Another object of the present invention is to provide a medical cart which is compact and lightweight for convenience in shipping.

Another object of the present invention is to provide a medical cart which can have drawers thereof pre-loaded with supplies suitable to allow the medical cart to function in different pre-defined ways, and with a cabinet of the medical cart being transitioned between a collapsed configuration and a deployed configuration with the collapsed configuration having a smaller volume than the deployed configuration, and with the drawers loading within the cabinet when the cabinet is in its deployed configuration.

Another object of the present invention is to provide a cart and method which can be printed from a selected printer data file, such as to cut, perforate or otherwise act on cardboard or other material to turn raw sheets of material into a deployable print on demand medical cart.

Another object of the present invention is to provide a cart which is suitable for emergency and/or disaster response and to enhance preparedness.

Another object of the present invention is to provide a medical cart which can be pre-sterilized and individually aseptically packaged and which is anti-microbial/anti-bacterial in nature.

Another object of the present invention is to provide a medical cart which is assigned to a single patient in a hospital or other environment of care (EOC) to minimize contamination risk and/or to facilitate billing/charging the cart expense to the care of the treated patient.

Other further objects of the present invention will become apparent from a careful reading of the included drawing figures, the claims and detailed description of the invention.

BRIEF DESCRIPTION OF THE DRAWINGS

FIG. 3 is a front elevation view of that which is shown in FIG. 1, and with the topper removed.

FIG. 4 is a rear elevation view of that which is shown in FIG. 3.

FIG. 5 is a left side elevation view of that which is shown in FIG. 3.

FIG. 6 is a right side elevation view of that which is shown in FIG. 3.

FIG. 9 is a perspective view of a wheeled base providing an alternative to the wheel assemblies of the example embodiment of FIGS. 1-8.

FIG. 10 is a perspective view from below of the wheeled base of FIG. 9 and with a cart including a cabinet and drawers similar to the example embodiment of FIG. 1, shown resting upon the wheeled base.

FIG. 14 is a perspective view of an alternative embodiment semi-automatic pop-up cart having a similar shape to the example cart of FIG. 1 after transitioning into its deployed configuration, and depicted in a collapsed substantially flat configuration before deployment.

FIG. 15 is a perspective view of that which is shown in FIG. 14 after partial deployment thereof.

FIG. 16 is a perspective view of that which is shown in FIG. 14 after full deployment and with a rear wall beginning a closing process to complete a cabinet of the cart for use.

FIG. 17 is a perspective view of that which is shown in FIG. 14 after full deployment and completion of the cabinet for use.

FIG. 18 is a perspective view of that which is shown in FIG. 14 after full deployment and completion of the cabinet for use, and with insertion of drawers into recesses in the cabinet and attachment of wheel assemblies.

FIG. 19 is a perspective view of an alternative embodiment semi-automatic pop-up drawer for use with the cart of FIG. 14 and depicted in a collapsed embodiment as a semi-automatic pop-up drawer for use with the cart of FIG. 14, and depicted in a collapsed substantially flat configuration before deployment.

FIG. 20 is a perspective view of that which is shown in FIG. 19 after partial deployment thereof.

FIG. 21 is a perspective view of that which is shown in FIG. 19 after full deployment and with a floor beginning a closing process to complete the drawer of the cart for use.

FIG. 22 is a perspective view of that which is shown in FIG. 19 after full deployment and after completion of the drawer for use by closing of the floor.

FIG. 23 is a perspective view of a spring loaded hinge structure locatable at one or more joints and or corners in the cabinet of FIGS. 14-18 or drawer of FIGS. 19-22, with springs therein configured to power automatic deployment of the cabinet and/or drawer between a collapsed configuration and a deployed configuration, for at least semi-automatic pop-up transition of the cabinet and/or drawer between a collapsed and a deployed configuration.

DESCRIPTION OF THE PREFERRED EMBODIMENT

Figure 11:
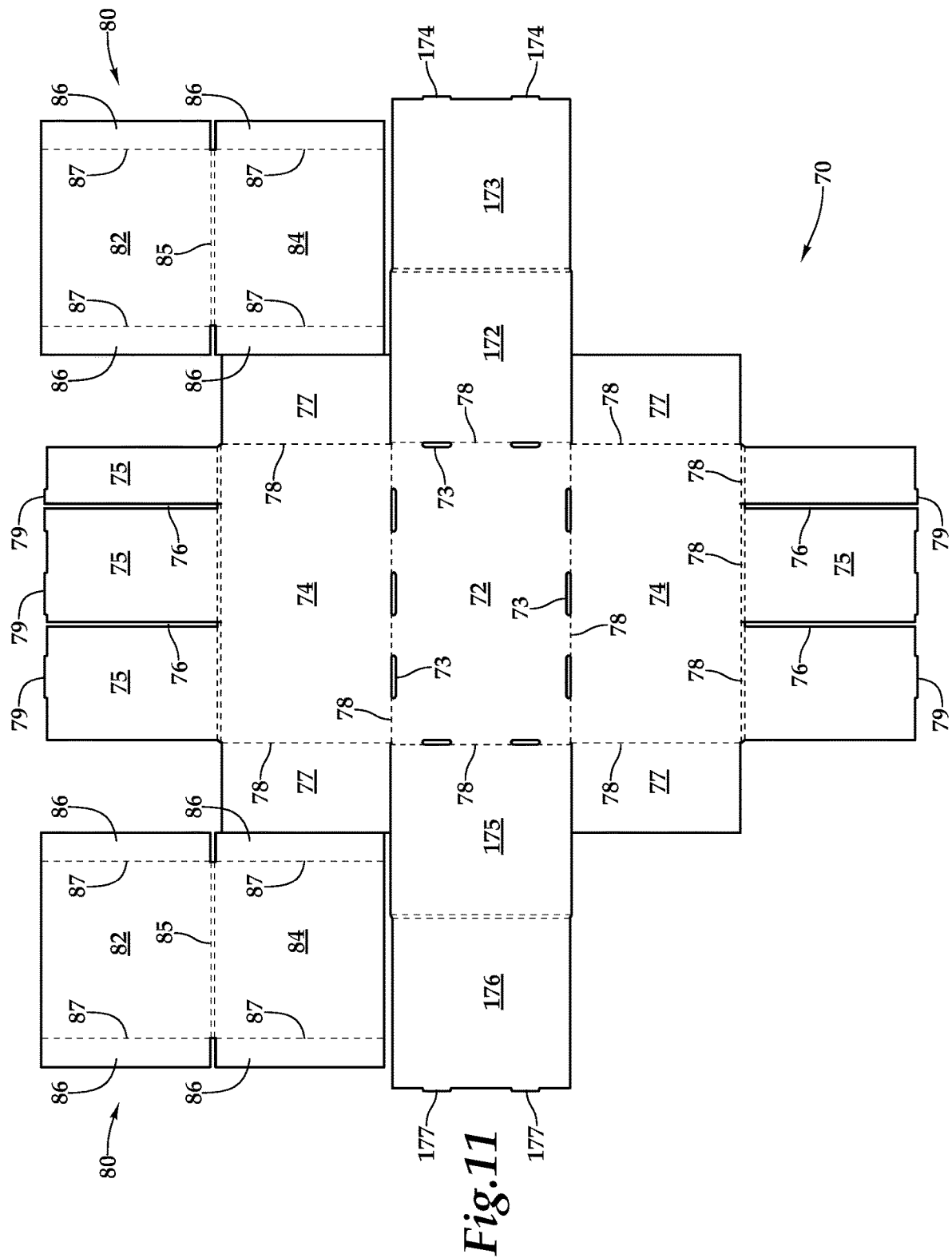
FIG. 11 is a top plan view of a cabinet sheet with cutouts and creases strategically located to allow for folding of various walls, layers and plates about various creases to facilitate construction of the cabinet of the cart, such as the example cart of FIG. 1.
Figure 12:
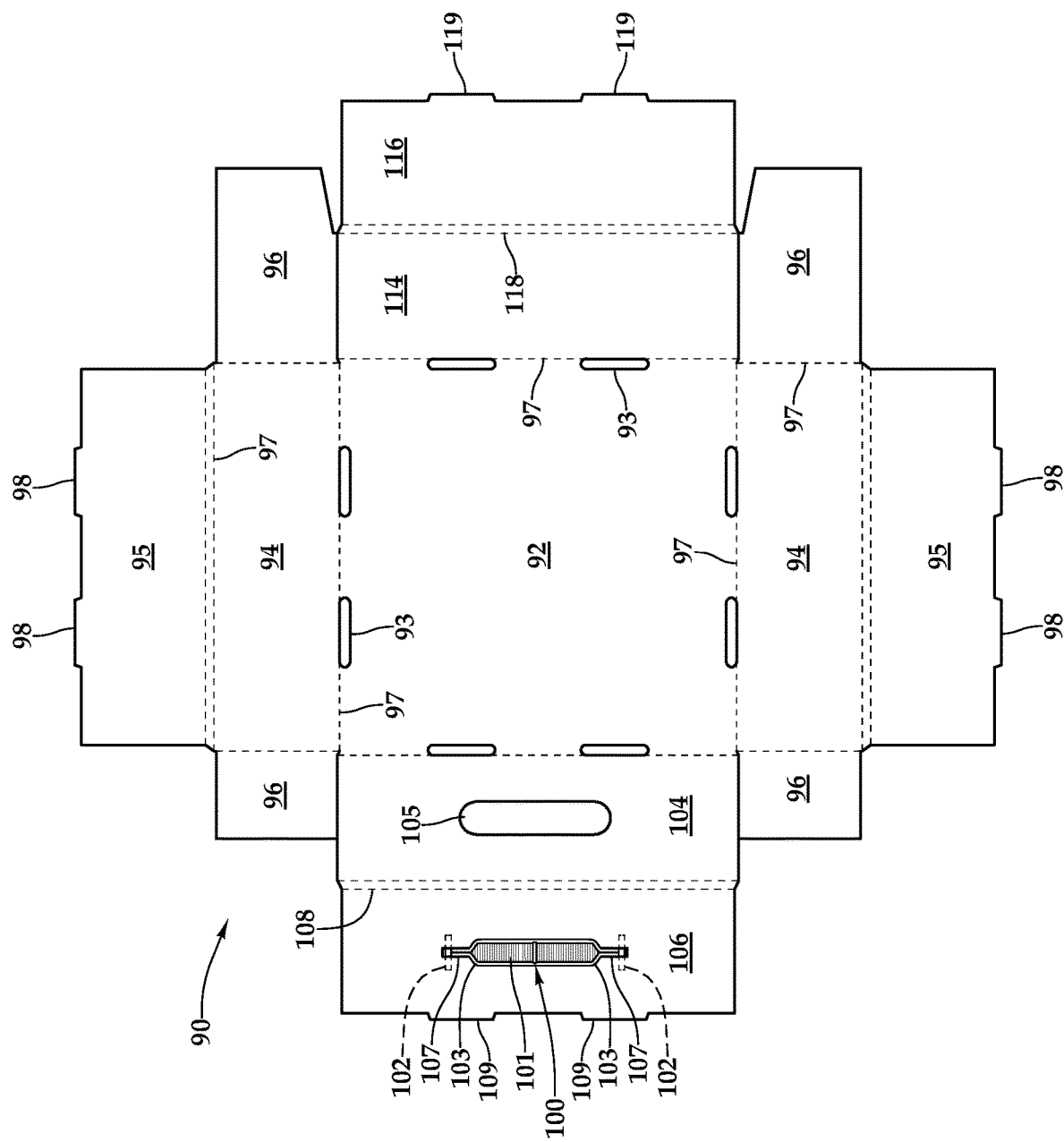
FIG. 12 is a top plan view of a small drawer sheet with cutouts and creases strategically located to allow for folding of various walls and layers about various creases to facilitate construction of a small drawer such as the small drawer in the example cart of FIG. 1.
Figure 13:
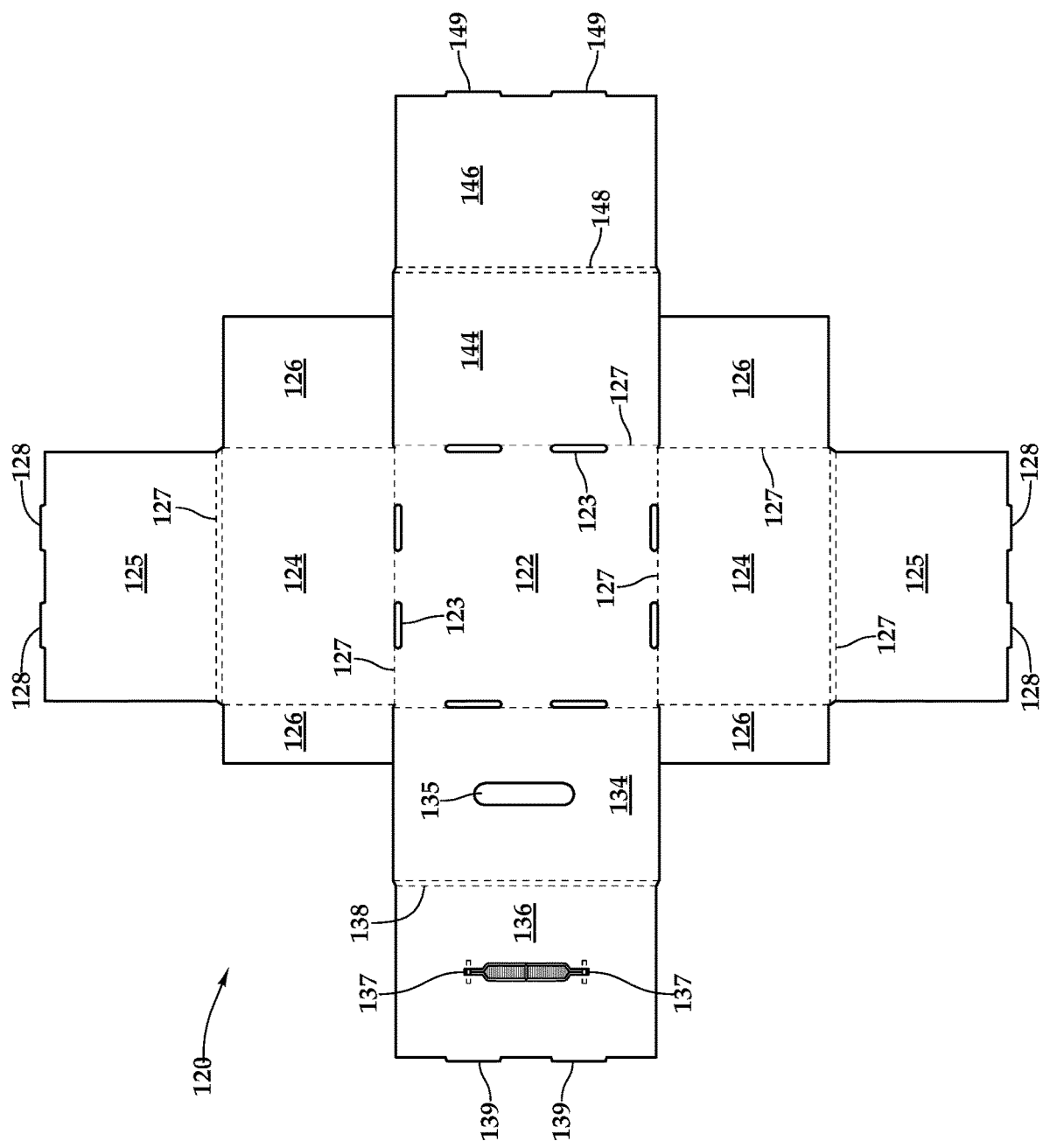
FIG. 13 is a top plan view of a large drawer sheet with cutouts and creases strategically located to allow for folding of various walls and layers about various creases to facilitate construction of a large drawer such as the large drawer in the example embodiment of FIG. 1.

Referring to the drawings, wherein like reference numerals represent like parts throughout the various drawing figures, reference numeral 10 is directed to a disposable pop-up single use medical cart (FIG. 1) which can be shipped and/or stored while collapsed flat and then erected into a deployed form, from sheets of material such as a cabinet sheet 70 (FIG. 11) and drawer sheets 90, 120 (FIGS. 12 and 13). In one embodiment, the cart can be configured as an automatic pop-up cart 200 to assist in deployment of the cart 200 and drawers 250.

Figure 2:
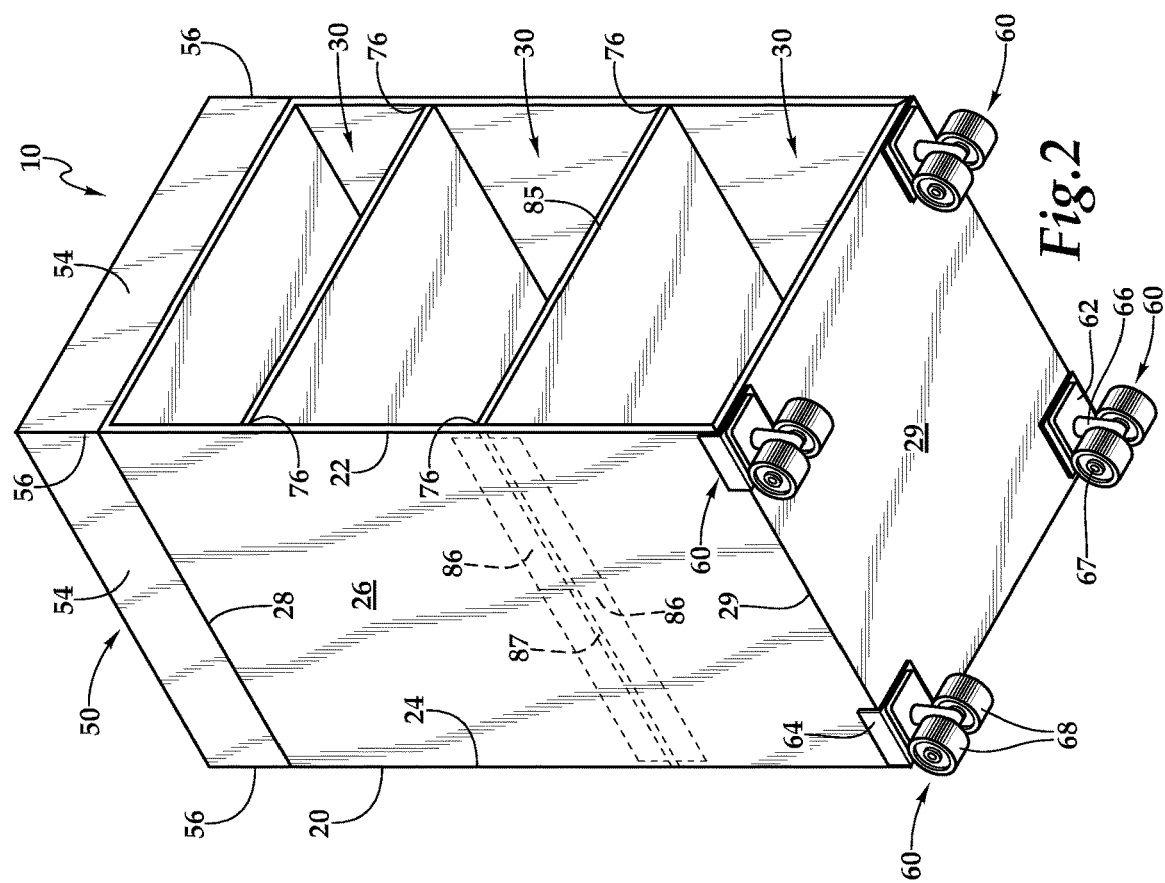
FIG. 2 is a perspective view from below of that which is shown in FIG. 1, and with the drawers removed, and with shelf details at least partially shown in broken lines where hidden within sides of the cabinet.
Figure 1:
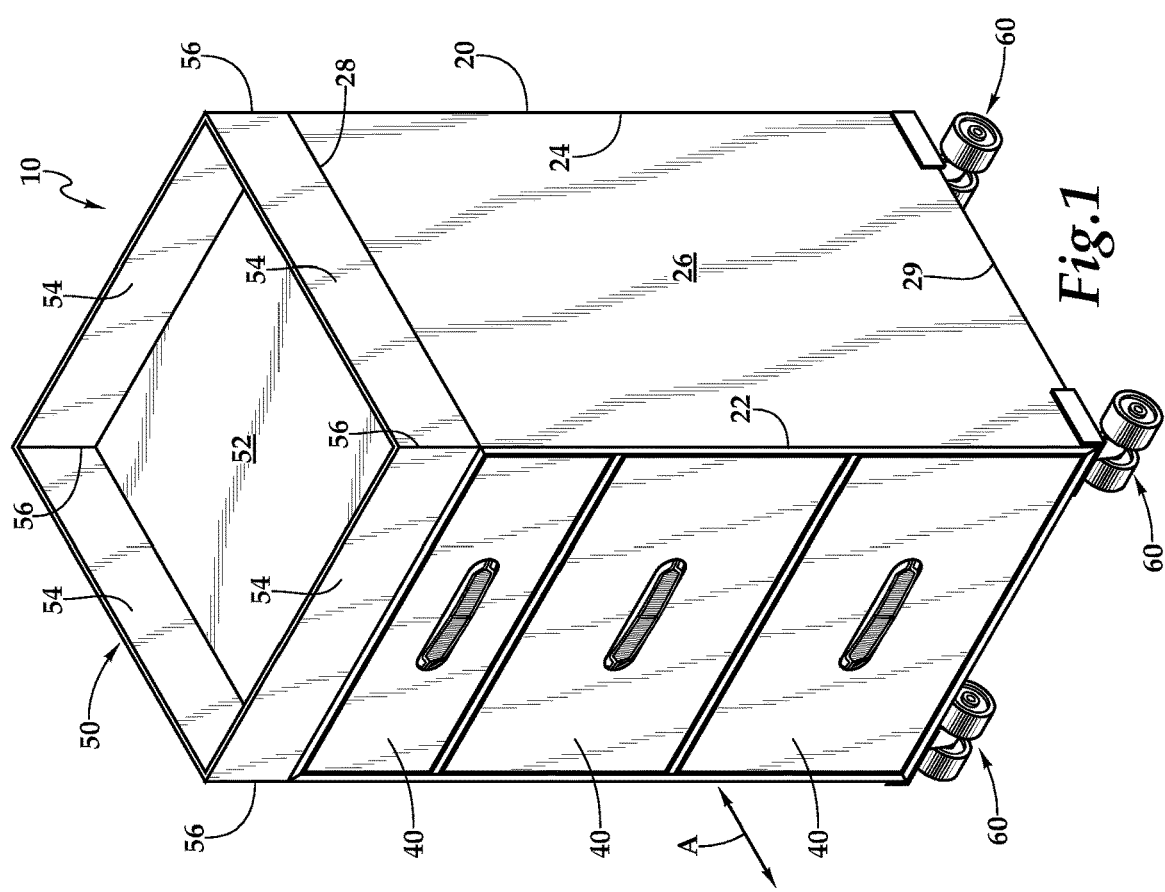
FIG. 1 is a perspective view of the medical cart according to an example embodiment of this invention, and including an optional topper structure resting upon a top of a cabinet of the cart, and with drawers of the cart located within recesses within the cabinet, and with the cabinet including optional wheel assemblies at corners of a bottom of the cabinet of the cart.
Figure 8:
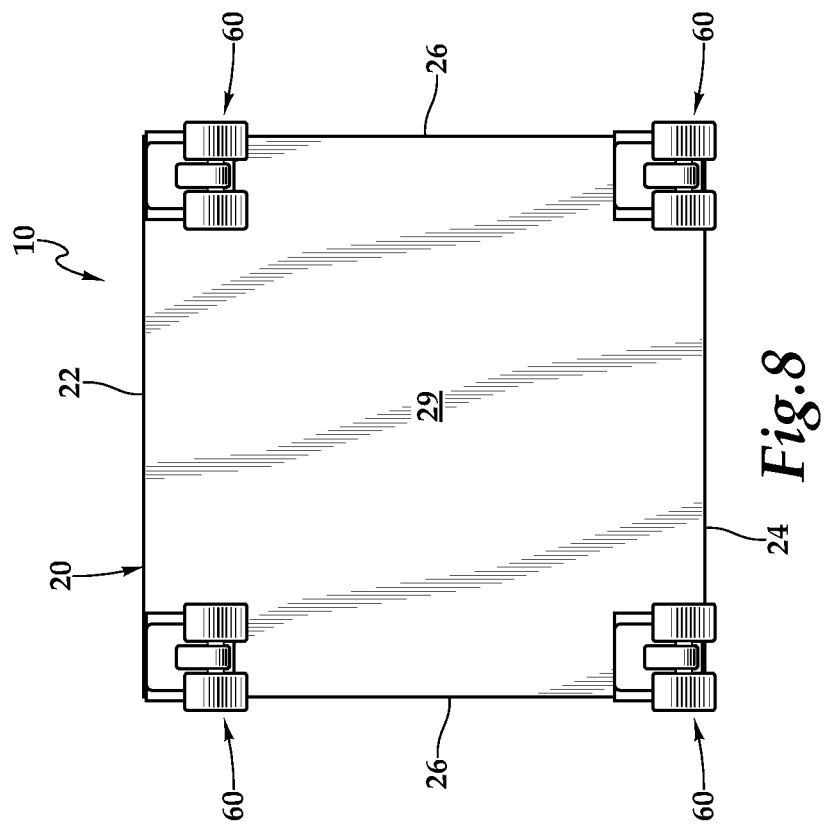
FIG. 8 is a bottom plan view of that which is shown in FIG. 3.
Figure 7:
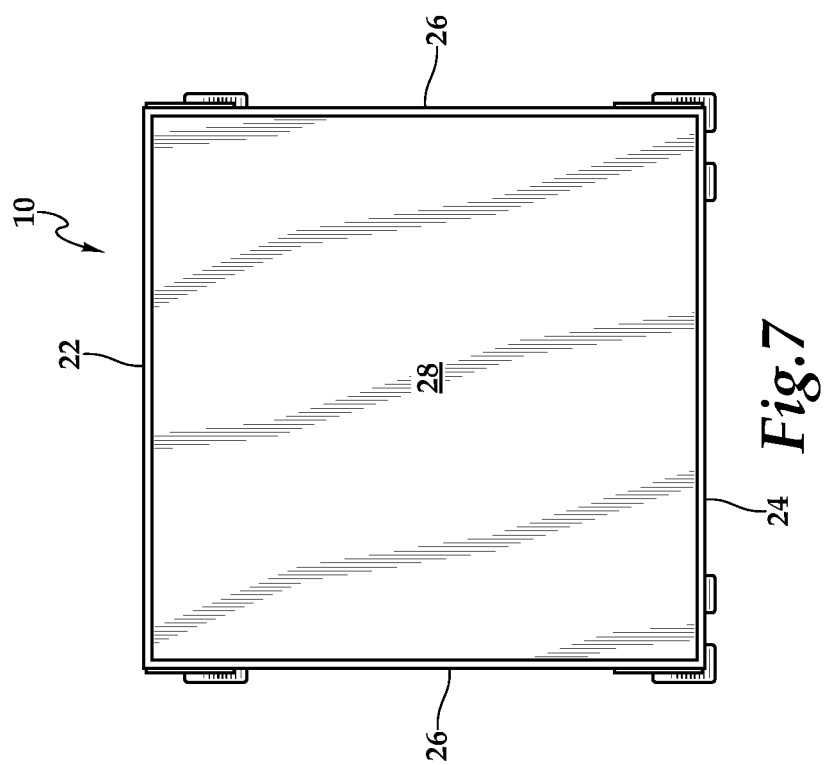
FIG. 7 is a top plan view of that which is shown in FIG. 3.

In essence, and with particular reference to FIGS. 1 and 2, basic details of the cart 10 are described, according to an example embodiment. The cart 10 includes a cabinet 20 with multiple recesses 30 therein. Separate drawers 40 fit within the recesses 30, which can include small drawers 40 for small recesses 30 and large drawers 40 for large recesses 30. A topper 50 can optionally be provided upon the cabinet 20 to help contain items placed upon the cart 10. Wheel assemblies 60 attach to an underside of the cabinet 20 to allow the cabinet 20 to roll upon an underlying surface, according to one embodiment. The cabinet 20 is formed (with reference to FIGS. 11-13) from a cabinet sheet 70 by folding of various portions of the cabinet sheet 70 relative to each other to result in providing a front 22, rear 24, sides 26, top 28 and bottom 29 of the cabinet 20. Shelf portions 80 are also provided within the cabinet sheet 70 which divide the front 22 of the cabinet 20 into separate recesses 30. A small drawer sheet 90 and large drawer sheet 120 can have portions thereof folded relative to each other to erect a small drawer 40 and multiple large drawers 40 (as an example). Handles 100 can be attached to these drawers 40 formed from the small drawer sheet 90 and/or large drawer sheet 120. An optional wheeled base 160 can be provided upon which the cabinet 20 rests, and which supports multiple wheel assemblies 60 (FIGS. 9 and 10).

In one embodiment, the cabinet sheet 70 is partially assembled in advance, but still allows the cabinet 20 to be provided in a collapsed substantially flat initial orientation. A user can simply apply rotating forces to various different panels, walls and/or layers to at least partially complete the deployment process for the cabinet 20. The drawers 40 an be similarly configured to "pop-up" from a collapsed initial configuration into a deployed final configuration. Such deployment is depicted in FIGS. 14-22, and can be at least partially automated by spring-loaded hinges, such as that depicted in FIG. 23.

More specifically, and with particular reference to FIGS. 1 and 2, details of a shape of the cabinet 20 when in a deployed configuration are described, according to this example embodiment. The cabinet 20 is a generally orthorhombic structure which is closed on all sides except for a front 22 of the cabinet 20 which in this embodiment is open in the form of recesses 30 which can receive drawers 40 with the cabinet 20 (or merely provide shelves). The cabinet 20 includes the open front 22 opposite and parallel with a planar rear 24. Two sides 26 are provided lateral to the front 22 and rear 24, which are parallel with each other and oriented within vertical planes. A top 28 is provided in a horizontal plane at upper ends of the sides 26 and front 22 and rear 24. A bottom 29 is provided which is parallel with the top 28 and defining a lower portion of the cabinet 20.

The front 22, rear 24, sides 26, top 28 and bottom 29 can be generally referred to as panels or walls or layers. In one embodiment, these panels are formed of cellulose material such as cardboard including typically multiple planar layers of craft paper with at least one fluted layer between outer planar layers. By utilizing such a cardboard material or other cellulosic material, biodegradability, compostability and a generally disposable nature is provided for the overall cart 10, or at least cabinet 20 portions of the cart 10 and drawer 30 portions of the cart 10 (other than handles 100 of the drawers 30 if such handles 100 are not formed of similar materials).

In other embodiments, these panels can be formed of other materials including plastics, composites, wood, metal, or other materials. While at least some joints between adjacent panels are continuous and merely formed by scoring, creasing, perforating, or otherwise providing strategically located linear zones of weakness within a larger planer structure, as an alternative, hinges of the same or different materials can be provided between such panels to facilitate pivoting therebetween.

The cart 10 can have any of various different sizes to be optimally sized for use. Most typically, the cart 10 has a size which places the top of the cabinet 20 at a comfortable height for a working surface for a standing individual working next to the cart 10. In alternative embodiments, the cart 10 could be shorter, such as to be at a convenient height to reach items placed upon the top 28 of the cabinet 20 when an individual is resting within a bed, such that the cart 10 can carry items which a patient in a bed might need to access without getting out of the bed.

While this embodiment includes three recesses 30 with three drawers 40, including an upper recess 30 for a small drawer 40 and two lower recesses 30 for two large drawers 40, different numbers and sizes of recesses 30 and corresponding drawers 40 could alternatively be provided. It is also conceivable that some drawers 40 could be left out, so that shelving would be provided within the cabinet 20 as part of the cart 10, in at least one embodiment doors could optionally close off space above such shelving, such doors hinged to an adjacent panel at one edge.

The drawers 40 are preferably sized to fill the recesses 30 and generally include a planar floor and with front and rear walls which are parallel to each other and oriented vertically, along with a pair of lateral walls spaced apart from each other and oriented vertically, to complete the drawer 40, and leaving an upper portion of the drawer 40 open. A handle 100 is preferably attached to each drawer 40. While the drawers can be erected from a collapsed form to a deployed form similar to the cabinet 20, as an alternative, the drawers 40 could be pre-deployed and pre-loaded with supplies for using the cart 10 for various different purposes. For instance, the drawers 40 could be pre-loaded with personal protective equipment (PPE), with the drawers 40 ready to be loaded into recesses 30 within the cabinet 20 after the cabinet 20 is deployed. As a further alternative, contents for drawers 40 of various different special-purpose carts 10 could be pre-packaged in modules which are sized to drop into the drawers 40 after the drawers 40 are deployed from their collapsed orientation. For instance, sets of personal protective equipment can be closed within sanitary plastic and present a module sized similar to an interior of one of the drawers 40 of the cart 10. Loading of the drawers 40 of the cart 10 and utilization of all of the space within the cart 10 is thus facilitated.

FIGS. 3-8 show the cart of FIGS. 1 and 2 from various orthogonal views. In these views, the topper 50 is removed so the details of the cabinet 20 can better be seen. In this embodiment, a width and depth of the cart are similar to each other and a height of the cart 10 is greater than the width. In other embodiments, the width of the cart can be greater than the depth of the cart (or vice versa) and the height of the cart 10 could conceivably be less than a width and/or depth of the cart 10. The drawers 40 slide out horizontally (along arrow A of FIG. 1) to allow an open top of each drawer 40 to be accessed for insertion of contents into the drawers for the removal of contents from the drawers 40.

A topper 50 is provided in the embodiment of FIGS. 1 and 2. This topper 50 is a separate structure including a planar surface 52 and with rim walls 54 extending upward from a perimeter of the surface 52. Corners 56 are provided between the rim walls 54. The topper 50 in this embodiment has a size and shape similar to that of the top 28 of the cabinet 20. Rim walls 54 allow items to be placed upon the surface 52 of the topper 50 and avoid rolling off, sliding off or otherwise coming off of the cart 10 by containment action of the rim walls 54. If desired, an adhesive or some fastener could be provided between the topper 50 and the top 28 of the cabinet 20 to permanently or temporarily attach the topper 50 to the cabinet 20 of the cart 10. As an alternative, the topper 50 could merely rest upon the cabinet 20 and be removable relative to the cabinet 20. The cart 10 could also be used without the topper 50. Most preferably, the topper 50 then be collapsed by having the rim walls 54 initially planar with the surface 52, and then pivoted relative to the surface 52 by 90°, and with the rim walls 54 joined at the corners 56 to complete the topper 50. The topper 50 can be formed of similar materials from which the cabinet 20 is formed, and/or from which the drawers 40 are formed, or can be formed of different materials. As one option, the topper is merely a planar sheet of rigid material, such as plastic.

With particular reference to FIG. 2, details of the wheel assemblies 60 are described, according to one embodiment. Each wheel assembly 60 includes a base plate 62 perpendicular to a side plate 64. These plates 62, 64 are planar and configured to abut and attach to the bottom 29 and sides 26 of the cabinet 20 at lower edges of the cart 20. The base plate 62 includes a hub extension 66 extending downwardly therefrom, which rotatably supports an axle 67 and with a pair of wheels 68 on the axle 67. The hub extension 66 also preferably swivels about a vertical axis, so that the wheels 68 and wheel assemblies 60 act as caster wheels which can swivel to allow rolling in various different directions.

These wheel assemblies 60 (also called wheel modules) provide one configuration for supporting a lower portion of the cabinets 20 defined by the bottom 29, and the lower portion of the cart 10 upon an underlying surface. In an alternative embodiment, the wheel assemblies 60 could be omitted, and the cart 10 could merely be moved about by sliding of the bottom 29 of the cabinet 20 upon an underlying surface. A coating or material characteristics of the bottom 29 could be configured to exhibit an appropriate coefficient of friction to provide a desirable compromise between ease of sliding of the cart 10 and minimization of unintended movement of the cart 10. As another option, other forms of wheel assemblies could be provided or variations to the wheel assembly 60 could be provided in alternative embodiments. While four wheel assemblies 60 are shown, a larger or smaller number of wheel assemblies 60 could be provided. While the wheel assemblies 60 are shown at corners of the bottom 29 of the cabinet 20 of the cart 10, wheel assemblies 60 could be provided at other locations, such as at midpoints of lower edges of the bottom 29 of the cabinet 20.

The wheel assemblies 60 can be attached through utilization of an adhesive, or other fasteners. Preferably, each wheel assembly 60 can be easily attached to the bottom 29 of the cabinet 20. In this way, when the cabinet 20 is being deployed from a collapsed form to a deployed form, the wheel assemblies 60 can be separately provided and attached to the cabinet 20 to quickly and easily complete deployment of the cabinet 20 of the cart 10.

With particular reference to FIGS. 9 and 10, details of a wheeled base 160 described, which provide a further alternative to the wheel assemblies 60. The wheeled base 160 includes a frame with multiple wheel assemblies 60 affixed to lower portions of the frame. The frame of the wheeled base 160 includes a ledge 162 of generally planar horizontal form, and with a rear curb 166 and a pair of side curbs 164 extending up from the ledge 162 at outer edges of the ledge 162. A front lip 168 which is shorter than the curbs 164, 166 extends up from a forward portion of the ledge 162. While the ledge 162 could be a complete plate, most preferably the ledge 162 is open at a central portion thereof, such as to minimize weight. The wheeled base 160 is sized so that the bottom 29 of the cabinet 20 can drop down onto the ledge 162 and in board of the curbs 166, 164 and in board of the front lip 168, with a front 22 of the cabinet 20 adjacent to the front lip 168, so the cabinet 20 can easily be located to rest upon and be supported upon the wheeled base 160. If desired, fastener could be utilized to hold the wheeled base 160 to the cabinet 20.

Multiple wheeled bases 160 could be provided, such as stacked one on top of the other, in a fairly compact form. The wheeled bases 160 could be formed of a plastic or metal material which is preferably autoclavable or otherwise sterilizable without damage to the wheeled base 160. In this way, the wheeled base 160 can be of a repeated use construction, while the cabinet 20 can be single use and disposable. Because the wheeled base 160 is adjacent to a floor which is generally a low sanitization surface, less than perfect sterilization of the wheeled base 160 could be acceptable in many medical environments.

With reference to FIG. 11, details of a cabinet sheet 70 of planar form are described, which has been pre-cut and creased/perforated to form the cabinet 20, as described according to one example embodiment. The cabinet sheet 70 includes a rear wall 72 (also called a rear wall panel) at a central portion thereof relative to which the other layers, panels, walls can be pivoted to complete construction of the cabinet 20 (FIGS. 1 and 2). The rear wall 72 is bounded by creases 78 and with tab slots 73 strategically located along portions of the creases 78. A pair of sidewall outer layers 74 (also called sidewall panels) are provided on opposing sides of the rear wall 72. Each sidewall outer layer 74 has a sidewall inner layer 75 on the side of the sidewall outer layer 74 opposite the rear wall 72. These sidewall inner layers 75 include sidewall slots 76 therein, strategically located to support shelves which divide the front 22 of the cabinet 20 into separate recesses 30.

The sidewall outer layers 74 also have sidewall wing tabs 77 extending from opposing sides of the sidewall outer layer 74. These wing tabs 77 can be tucked between various top wall and bottom wall layers of the cabinet 20 to help hold the sidewall outer layer 74 and sidewall inner layer 75 in deployed position within the cabinet 20. Tabs 79 on portions of the sidewall inner layer 75 opposite the sidewall outer layer 74 are located and sized to fit into the tab slots 73 after the sidewall inner layer 75 is doubled back 1800 relative to the sidewall outer layer 74, to complete assembly of the sides 26 of the cabinet 20.

The cabinet sheet 70 also includes a top wall outer layer 172 opposite a bottom wall outer layer 175 (also called a lower shelf panel). The top wall outer layer 172 have the top wall inner layer 173 on a side of the top outer layer 172 opposite the rear wall 72. The bottom wall outer layer 175 supports a bottom wall inner layer 176 on an end of the bottom wall outer layer 175 opposite the rear wall 72. Tabs 174 are located on a portion of the top wall inner layer 173 opposite the top wall outer layer 172. Similarly, tabs 177 extend from an edge of the bottom wall inner layer 176 opposite the bottom wall outer layer 175. These tabs 174, 177 fit into tab slots 73 adjacent to the rear wall 72, to complete the double wall construction of the top 28 and bottom 29 of the cabinet 20, after the inner layers 173, 176 are doubled back 1800 adjacent to the outer layers 172, 175.

To complete the cabinet 20, multiple shelf portions 80 (also called additional shelf panels) are provided, which are depicted in this example environment within FIG. 11 cut from a common original cabinet sheet 70. The shelf portions 80 are cut to be entirely separable from other portions of the cabinet sheet 70. Each shelf portion 80 includes a first plate 82 and second plate 84 with a fold line 85 between these plates 82, 84. Wings 86 extend laterally from the first plate 82 and second plate 84 with the wings 86 including creases 87 where the wings 86 are joined to the plate 82, 84. As depicted in FIG. 2 in broken lines, after the first plate 82, 84 fold over 180° to be parallel to each other about the fold line 85, the wings 86 can bend 900 about the creases 87 to extend upwardly and downwardly and be nested between the sidewall outer layer 74 and the sidewall inner layer 75, when edges of the shelf portion 80 are fit within the sidewall slots 76. The shelves 80 divide the front 22 of the cabinet 20 into separate recesses 30, divided by the shelf portions 80 at the location of the sidewall slots 76 of the cabinet sheets 70.

With particular reference to FIG. 12, a small drawer sheet 90 can initially be provided in one embodiment which can be erected to transition a drawer 40 from a collapsed form, such as that depicted in FIG. 11, and into a deployed form, such as that depicted in FIG. 1. In this embodiment, the small drawer sheet 90 includes a floor 92 (also called a floor panel) as a central element about which other portions of the drawer 40 bend to erect the drawer 40 from the small drawer sheet 90. Portions of the small drawer 90 adjacent to the floor 92 include two opposite lateral wall outer layers 94 (also called side panels). The lateral wall outer layers 94 include a lateral wall inner layer 95 at a portion of the lateral wall outer layer 94 opposite the floor 92. The lateral wall outer layer 94 includes lateral wall wing tabs 96 extending in opposing directions from the lateral wall outer layer 94. These lateral wall wing tabs 96 can be tucked between portions of the front and rear of the drawers 40, partly during construction into the deployed configuration for the drawers 40. Creases 97 join the various layers to each other and to the floor 92. Tabs 98 at extreme edges of the lateral wall inner layers 95 can fit into the tab slots 93 the lateral wall inner layer 95 is pivoted 1800 relative to lateral wall outer layer 94.

Handles 100 are provided on front portions of each drawer 40 in this example embodiment. Each handle 100 includes a central pull 101 and with a pair of necks 103 terminating at tee tips 102. The small drawer sheet 90 includes a front wall outer layer 104 (also called a front panel) extending from one side of the floor 92. A port 105 is formed in the front wall outer layer 104, sized large enough for the pull 101 of the handle 100 to pass therethrough. A front wall inner layer 106 is attached to a portion of the front wall outer layer 104 opposite the floor 92 through a crease 108. Slits 107 are formed on the front wall inner layer 106. These slits 107 are small enough to keep the pulls 101 from passing through the slits 107, but large enough to allow the necks 103 to pass through the slits 107. The tee tips 102 can thus be anchored through the slits 107 and with the pulls 101 of the handles 100 accessed through the ports 105. Tabs 109 at extreme edges of the front wall inner layer 106 fit into the tab slots 93 at edges of the floor 92 to hold the front wall inner layer 106 parallel with and inboard of the front wall outer layer 104, to complete the front of the drawer 40.

A rear wall outer layer 114 (also called a rear panel) extends from the floor 92 on a side of the floor 92 opposite the front wall outer layer 104. A rear wall inner layer 116 extends from an edge of the rear wall outer layer 114 opposite the floor 92. Creases 118 are located between the rear wall outer layer 114 and rear wall inner layer 116, to allow for the rear wall inner layer 116 to be bent 180° relative to the rear wall outer layer 114. Tabs 119 on extreme edges of the rear wall inner layer 116 can tuck into the tab slots 93 adjacent to the floor 92 to complete construction of the rear of the drawers 40. The lateral wall wing tabs 96 fit between the rear wall outer layer 114 and rear wall inner layer 116 to hold corners of the drawer 40 together.

With particular reference to FIG. 13, details of a large drawer sheet 120 which can be erected into a large drawer 40 (FIG. 1) are described, according to this example embodiment. A large drawer sheet 120 is preferably similar to the small drawer sheet 90, except that a height of the large drawer 40 formed from the large drawer sheet 120 is greater than the drawer 40 formed from the small drawer sheet 90. The large drawer sheet 120 includes a floor 122 bounded by tab slots 123 and with a lateral wall outer layer 124 and lateral wall inner layer 125 joined together across a crease 127, and with lateral wall wing tabs 126 connected through creases 127 to the lateral wall outer layer 124. Tabs 128 are provided at tips of the lateral wall inner layer 125 to fit into the tab slots 123.

A front wall outer layer 134 is provided with a port 135 therein for supporting a handle 100 passing therethrough. A front wall inner layer 136 is preferably attached by a crease 137 to the front wall outer layer 134. Slits 137 in the front wall inner layer 136 hold the handles 100 relative to the front of the drawer 40. Tabs 139 at extreme ends of the front wall inner layer fit into the tab slots 123 adjacent to the floor 122. A rear wall outer layer 144 is joint through creases 148 to a rear wall inner layer 146. Tabs 149 at an extreme edge of the rear wall inner layer 146 fit into the tab slots 123 adjacent to the floor 122. Thus, a drawer 40 can also be formed from the large door sheet 120 in a manner similar to formation of a drawer 40 from the small drawer sheet 90, as described above.

While the various sheets 70, 90, 120 include a particular arrangement of various different layers forming the different portions of the cart 10, other configurations could alternatively be provided for the sheets 70, 90, 110. For instance, rather than the rear wall 72 providing a central base portion of the cabinet sheet 70, some other portion of the cabinet 20 could be provided as such a base portion of an alternative cabinet sheet. Similarly, the drawer sheets 90, 120 could have some portion of a drawer 40 other than floors 92, 122 function as a central base portion for construction of the drawers 40 from the sheets 90, 120.

In one embodiment depicted in FIGS. 14-18, the cabinet 200 is provided of an at least partially automatic pop-up variety. The pop-up cart 200 begins as a collapsed cart 210 (FIG. 14). In this initial collapsed form, a top and one side wall face the viewer. A rear wall 235 also faces the viewer. Joints between the top, sidewall and rear wall are pivotable 90°. A second side wall and floor face away from the viewer in this figure and are parallel and nearly co-planar with the forward facing top and side wall. Shelves which space recesses apart are located between these two sidewalls.

As shown in FIG. 15, pop-up deployment of the collapsed cart 210 occurs by transition into the partially expanded cart 215 shown in FIG. 15. The partially expanded cart 215 has had a bottom of the partially expanded cart 215 pivoted (along arrow B of FIG. 15) at least somewhat, so that the bottom wall of the partially expanded the cart 215 is angled between 0° and 90° away from the sidewall which is facing the viewer. As such expansion occurs, details of the partial expanded cart 215 can be seen, including edge joints 240 and junction joints 245. These joints 240 have two panels coming together at edges of the cart 200, while junction joints 245 have a shelf panel joined at a midpoint of a sidewall.

As shown in FIG. 16, full rotation beyond that depicted in FIG. 15 results in the top and bottom of the deployed cart 220 oriented perpendicular to the sidewalls. In FIG. 16 the rear wall 235 is beginning to pivot (along arrow C) to close off a rear of the pop-up cart 200. Tabs 237 on the rear wall 235 can be utilized for attachment and closure of the rear wall 235. Such closure and attachment rigidifies and supports the pop-up cart 200 in what is now the complete cart 230 depicted in FIG. 17. Drawers 250 and wheel assemblies 60 can then be added to complete the pop-up cart 200.

With particular reference to FIGS. 19-22, corresponding automatic pop-up drawer 250 is disclosed. Initially the drawer 250 is configured as a collapsed drawer 260 (FIG. 19). The drawer 250 then transitions through being a partial expanded drawer 265 (FIG. 20) and then into a deployed drawer 270 (FIG. 21) and finally as a complete drawer 280 (FIG. 22). When the drawer 250 is configured as the collapsed drawer 260 (FIG. 19), a front and sidewall of the drawer 250 face a viewer as well as a floor 275 of the drawer 250. A partially expanded drawer 265 (FIG. 20) has the front and side of the drawer 250 angling away from totally facing the viewer, and with an angular displacement shrinking from 180° down toward 90°. Other inside corners of the drawer 250 are expanding (along arrow D of FIGS. 20 and 21). The drawer 250 includes four edge joints 290 which pivot during this pop-up action. The drawer 250 is completed (FIG. 22) by pivoting of the floor 275 (along arrow F of FIG. 21) to a closed position.

Such pop-up action for deployment of the previously collapsed substantially flat pop-up cart 200 and associated pop-up drawer 250 can occur manually or automatically. For manual pop-up action, a user manually applies pivoting forces at appropriate joints 240, 245, 290 to cause conversion from the collapsed configuration to the deployed configuration. As an alternative, a spring or other biasing element can automate such deployment.

In particular, and as depicted in FIG. 23, a spring assembly 310 in the form of a hinge structure can be strategically located at one or more of the joints 240, 245, 290 to power such pop-up deployment and cause the pop-up deployment to be automatic in nature for the cabinet of the cart 200 and/or the drawer 250. The spring assembly 310 would be located at such a joint 240, 245, 290 such as positions depicted in FIG. 17, FIG. 21 and FIG. 22.

The spring assembly 310 includes a first plate 320 hinged to a second plate 330 through leaves 325, 335 pivotably mounted to a pintle 340. At least one torsion spring 350 acts on the plates 320, 330. The torsion springs 350 push or pull the plates 320, 330 into different positions relative to each other based on the orientation of the torsion spring 350 and the plates 320, 330. The torsion springs 350 can be configured to bias the spring assembly 310 to have a final 900 spacing between the first plate 320 and second plate 330.

The spring assembly 310 can be collapsed to be folded with the plates 320, 330 adjacent to each other and folded flat, where energy is stored in the torsion springs 350. The automatic pop-up cart 200 and/or automatic pop-up drawer 250 can be restrained in a collapsed form, such as by enclosure within wrapping, and with the torsion springs 350 in such a stored energy state. When the wrapping is removed, the energy in the torsion springs 350 is released, and automatic pop-up action occurs. A user would then manually close the rear wall 235 or floor 275 to complete the cart 200 or drawer 250.

As an alternative, a joint between the rear wall 235 and other portions of the cart 200 and/or a joint between the floor 237 and other portions of the drawer 250 could similarly be configured with a spring structure or other biasing structure like the spring assembly 310, so that the rear wall 235 and/or floor 275 could also automatically pivot to a final position. Such a configuration would provide a fully automatic pop-up cart 200 and fully automatic pop-up drawers 250. In such a configuration, little or no assembly effort is required to deploy and begin utilizing the cart 200 and associated drawers 250.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When embodiments are referred to as "exemplary" or "preferred" this term is meant to indicate one example of the invention, and does not exclude other possible embodiments. When structures are identified as a means to perform a function, the identification is intended to include all structures which can perform the function specified. When structures of this invention are identified as being coupled or attached together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A deployable medical cart, comprising in combination:
   a first sheet of planer material including a lower shelf panel, two side wall panels, at least one additional shelf panel, and a rear wall panel, each of said panels pivotable relative to other portions of said first sheet of planar material to construct a cabinet portion of the medical cart;
   a second sheet of planar material including a floor panel, two side panels, a front panel and a rear panel, each pivoted relative to other portions of said second sheet of planar material to construct at least one drawer of the medical cart;
   said drawer sized to fit between said two sidewall panels of said cabinet portion of the medical cart;
   a plurality of wheels rotatably supportable relative to a support structure, said support structure attachable adjacent to said lower shelf panel of said cabinet portion of the medical cart; and
   wherein at least two of said panels of said first sheet which are adjacent to each other include a spring loaded hinge therebetween, biased toward a deployed orientation of said at least two adjacent panels.

2. The medical cart of claim 1 wherein at least two of said panels of said first sheet of planar material are attached to each other on portions thereof which are spaced from said lower shelf panel so that they pivot simultaneously from a first collapsed orientation parallel with said lower shelf panel into a deployed orientation perpendicular to said lower shelf panel, such that the medical cart is deployed in an at least partially automated pop-up fashion.

3. The medical cart of claim 1 wherein said cabinet includes shelves which divide said cabinet into three recesses and wherein three drawers are provided from at least one separate sheet of planar material separate from said first sheet of planar material, each of said drawers fitting within one of said recesses of said cabinet.

4. The medical cart of claim 1 wherein said plurality of wheels include caster wheels which can both roll and pivot relative to said cabinet.

5. The medical cart of claim 1 wherein each of said planar sheets of material are formed of a similar sustainable material.

6. The medical cart of claim 5 wherein said sustainable material is a recyclable material.

7. The medical cart of claim 6 wherein said recyclable material is a recyclable plastic material.

8. The medical cart of claim 6 wherein said recyclable material is a recyclable cellulosic material.

9. The medical cart of claim 5 wherein said sustainable material is a biodegradable material.

10. The medical cart of claim 9 wherein said biodegradable material is a compostable cellulosic material.

11. The medical cart of claim 1 wherein said spring-loaded hinge includes a first plate pivotably attached to a second plate through a pintle, and wherein at least one torsion spring surrounds said pintle and bears upon said first plate and said second plate to bias said first plate and said second plate relative to each other, said first plate and said second plate attachable two different ones of said two adjacent panels of said first sheet.

12. The medical cart of claim 1 wherein said at least one drawer is pre-loaded with supplies.

13. The medical cart of claim 12 wherein said at least one drawer is pre-loaded with specialty content taken from the group of specialty content including:
   personal protection equipment, bedding, hygiene equipment and medical equipment and supplies.

14. A deployable medical cart, comprising in combination:
   a first sheet of planer material including a lower shelf panel, two side wall panels, at least one additional shelf panel, and a rear wall panel, each of said panels pivotable relative to other portions of said first sheet of planar material to construct a cabinet portion of the medical cart;
   a second sheet of planar material including a floor panel, two side panels, a front panel and a rear panel, each pivoted relative to other portions of said second sheet of planar material to construct at least one drawer of the medical cart;
   said drawer sized to fit between said two sidewall panels of said cabinet portion of the medical cart;
   a plurality of wheels rotatably supportable relative to a support structure, said support structure attachable adjacent to said lower shelf panel of said cabinet portion of the medical cart; and
   wherein at least two of said panels of said second sheet which are adjacent to each other include a spring loaded hinge therebetween, biased toward a deployed orientation of said at least two adjacent panels of said second sheet of planer material.

15. A method of deploying a collapsed medical cart including a cabinet and at least one drawer, the method including the steps of:

erecting a cabinet from a first sheet of planer material including a lower shelf panel, two side wall panels, at least one additional shelf panel, and a rear wall panel, each of said panels pivotable relative to other portions of said first sheet of planar material to construct a cabinet portion of the medical cart by pivoting the lower shelf relative to at least the two side walls;

erecting at least one drawer from a second sheet of planar material including a floor panel, two side panels, a front panel and a rear panel, each pivoted relative to other portions of said second sheet of planar material to construct at least one drawer of the medical cart by pivoting the floor panel relative to at least the two side panels;

placing the at least one drawer of said erecting at least one drawer step into the cabinet of said erecting a cabinet step; and wherein said erecting a cabinet step includes spring loading at least two of the panels of said first sheet of planar material which are adjacent to each other, to cause the at least two panels to move from a collapsed orientation to a deployed orientation.

16. The method of claim 15 including the further step of attaching a plurality of wheels adjacent to the lower shelf.

17. The method of claim 15 including the further step of placing the cabinet onto a wheeled base assembly, the wheeled base assembly having a plurality of wheels rotatably attached to a frame sized to receive the lower shelf of the cabinet therein.

18. A method of deploying a collapsed medical cart including a cabinet and at least one drawer, the method including the steps of:

erecting a cabinet from a first sheet of planer material including a lower shelf panel, two side wall panels, at least one additional shelf panel, and a rear wall panel, each of said panels pivotable relative to other portions of said first sheet of planar material to construct a cabinet portion of the medical cart by pivoting the lower shelf relative to at least the two side walls;

erecting at least one drawer from a second sheet of planar material including a floor panel, two side panels, a front panel and a rear panel, each pivoted relative to other portions of said second sheet of planar material to construct at least one drawer of the medical cart by pivoting the floor panel relative to at least the two side panels;

placing the at least one drawer of said erecting at least one drawer step into the cabinet of said erecting a cabinet step; and wherein said erecting at least one drawer step includes spring loading at least two of the panels of said second sheet of planar material which are adjacent to each other, to cause the at least two panels to move from a collapsed orientation to a deployed orientation.

\* \* \* \* \*